US 6,708,121 B2

(12) United States Patent
Arake et al.

(10) Patent No.: US 6,708,121 B2
(45) Date of Patent: Mar. 16, 2004

(54) ANALYZING APPARATUS (75) Inventors: Akira Arake, Ibaraki (JP); Hiroaki Kita, Osaka (JP); Yoshihisa Yamamoto, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 0 days.

(21) Appl. No.: 09/985,119

(22) Filed: Nov. 1, 2001

(65) Prior Publication Data

US 2002/0052695 A1 May 2, 2002

(30) Foreign Application Priority Data

Nov. 1, 2000 (JP) ........................................ 2000-334192

(51) Int. Cl.[7] .............................................. G01N 31/00
(52) U.S. Cl. ......................................... 702/31; 210/656
(58) Field of Search ........................... 702/31; 250/281; 714/22; 422/88; 210/656, 96.2

(56) References Cited

U.S. PATENT DOCUMENTS

| 3,890,494 | A | * | 6/1975 | Meshek et al. ................ 714/22 |
| 4,314,156 | A | * | 2/1982 | Kuppermann et al. ....... 250/281 |
| 5,011,608 | A | * | 4/1991 | Damjanovic ................. 210/656 |
| 5,597,535 | A | * | 1/1997 | Schaedlich et al. ........... 422/88 |
| 5,744,027 | A | * | 4/1998 | Connell et al. ............. 210/96.2 |

FOREIGN PATENT DOCUMENTS

| JP | 64-003716 | 1/1989 |
| JP | 11-083865 | 3/1999 |
| JP | 2000-200294 | 7/2000 |

OTHER PUBLICATIONS

Introduction of Fluorescence X–Ray Analyzer RIX3000 and RIX3001 by Rigaku Industrial Corporation, ESI–News vol. 14, No. 2, 1996.

* cited by examiner

Primary Examiner—John Barlow
Assistant Examiner—Xiuqin Sun
(74) Attorney, Agent, or Firm—Antonelli, Terry, Stout & Kraus, LLP (57) ABSTRACT An analyzing apparatus 1, such as a fluorescence X-ray analyzer, being able to analyze samples automatically, by transferring the samples into an analysis chamber, sequentially, comprising: an interruption recover device 11 for automatically turning on an electric power supply for the analyzing apparatus, when electricity is re-established after interruption thereof; and a data processing computer 2, being connected through the uninterruptible power source 3 to an electric power source, wherein, the data processing computer 2 includes function for temporality memorizing analysis information of the automatic analyzing apparatus when the interruption of electricity occurs, and function for supplying electricity to the analyzing apparatus 1 through the interruption recover device 11 and also for re-starting the analysis of the samples upon the basis of the memorized analysis information at the time when the interruption occurs, when the electricity is recovered, thereby being suitable for unmanned operation thereof.

3 Claims, 7 Drawing Sheets

| STATUS | OPERATION SQ | SAMPLE POSITION | ANALYSIS CODE | CONTENTS |
|---|---|---|---|---|
| 1 | 1 | 3 | ABC | QUANTITATIVE ANALYSIS OF STAINLESS STEEL |
| 1 | 2 | 4 | BCD | QUALITATIVE ANALYSIS OF POWDER SAMPLE |
| ... | ... | ... | ... | ... |
| ... | ... | ... | ... | ... |
| 0 | 12 | 5 | AAA | |

ANALYZING APPARATUS

BACKGROUND OF THE INVENTION

1. Field of the Invention

The present invention relates to an analyzing apparatus, including a fluorescence X-ray analyzer, with which fluorescence X-rays from samples are measured, so as to analyze the samples, etc., and in particular to an analyzing apparatus, in which the analysis will be conducted continuously when electricity is recovered, even if it is stopped or instantaneously interrupted during the use thereof.

2. Description of Prior Art

Conventionally, fluorescence X-ray analyzers, in which the fluorescence X-rays, being obtained from the samples irradiated with X-rays within a vacuum analysis chamber of a main body thereof, are measured so as to analyze them, are widely used due to high accuracy in analyzing ability thereof, for analyzing various sorts of materials in various technical fields. In such the fluorescence X-ray analyzers, for the purpose of automatic operation of analysis, an analyzing apparatus is already known, in which a large number of materials (i.e., samples) are analyzed while being transferred into and discharged from the analysis chamber of the fluorescence X-ray analyzer, sequentially, with using an automatic sample exchanger or the like, thereby achieving the automatic analysis of the samples.

Namely, the fluorescence X-ray analyzer, being able to perform analysis continuously for a long time, by using such the automatic sample exchanger as mentioned above, is normally connected to a host computer, which is provided separate from that apparatus, whereby an unmanned or automatic operation (analysis) is realized through instructions made by the host computer, as well as, the functions of an automatic sample handling mechanism constructing the automatic sample exchanger.

However, even with the analyzing apparatus being able to perform the unmanned operation, it stops the analysis operation, if once the power source of the apparatus stops the electricity (for example, for a time duration from about several tens min. to several hundreds sec.) and/or when it is interrupted simultaneously (for example, shorter than 1 min.) due to lightning, etc. However, for the analyzing apparatus stopping the operation once, it is impossible to recover the analyzing operation, automatically, back to that at the time point when it stops the operation. Therefore, the recovery of the analyzing apparatus when the electricity is recovered comes to be a big problem, in particular, for the analyzing apparatus being able to perform such the unmanned operation as mentioned above.

SUMMARY OF THE INVENTION

Then, according to the present invention, for dissolving such the drawbacks in the conventional technology as mentioned above, an object is to provide an analyzing apparatus, being able to perform the unmanned operation, wherein the apparatus starts the operation thereof by turning on a power source, automatically, when the electricity is recovered from, so as to re-establish or re-start the analysis operation back to that at the time when the power stoppage occurred, thereby ensuring continuity of the analysis operation.

Therefore, according to the present invention, for achieving the object mentioned above, there is provided an analyzing apparatus able to analyze samples automatically, by transferring the samples into an analysis chamber, sequentially, comprising: an interruption recovering means for automatically turning on an electric power supply for the analyzing apparatus, when electricity is re-establishing after interruption thereof; and a calculation processing portion, being connected through said interruption recovering means to said electric power source, wherein, said calculation processing portion includes means for temporality memorizing analysis information of said automatic analyzing apparatus when the interruption occurs, and further means for supplying electricity to said analyzing apparatus through said interruption recovering means and for re-starting the analysis of the samples upon basis of the memorized analysis information at the time when the interruption occurs, when the electricity is recovered.

Further, according to the present invention, in the analyzing apparatus as mentioned in the above, it is preferable that said calculation processing portion further comprises means for executing initialization of said automatic analyzing apparatus, after automatically turning on said electric power source onto said analyzing apparatus when the electricity is recovered, and said calculation processing portion further comprises means for conducting setting operation for said analyzing apparatus after execution of the initialization of said automatic analyzing apparatus.

Also, according to the present invention, in the analyzing apparatus as mentioned in the above, it is preferable that it further comprises an X-rays tube, and wherein said calculation processing portion further comprises means for executing aging of said x-rays tube after turning on said electric power source when the electricity is recovered after the interruption thereof.

BRIEF DESCRIPTION OF THE DRAWINGS

Those and other features, objects and advantages of the present invention will become more apparent from the following description when taken in conjunction with the accompanying drawings wherein:

FIG. 7 shows a flowchart for explaining the details of operations of power interruption-recovering processes when the electricity is recovered from.

DETAILED DESCRIPTION OF PREFERRED EMBODIMENTS

Hereinafter, embodiments according to the present invention will be fully explained by referring to the attached drawings.

Figure 2:
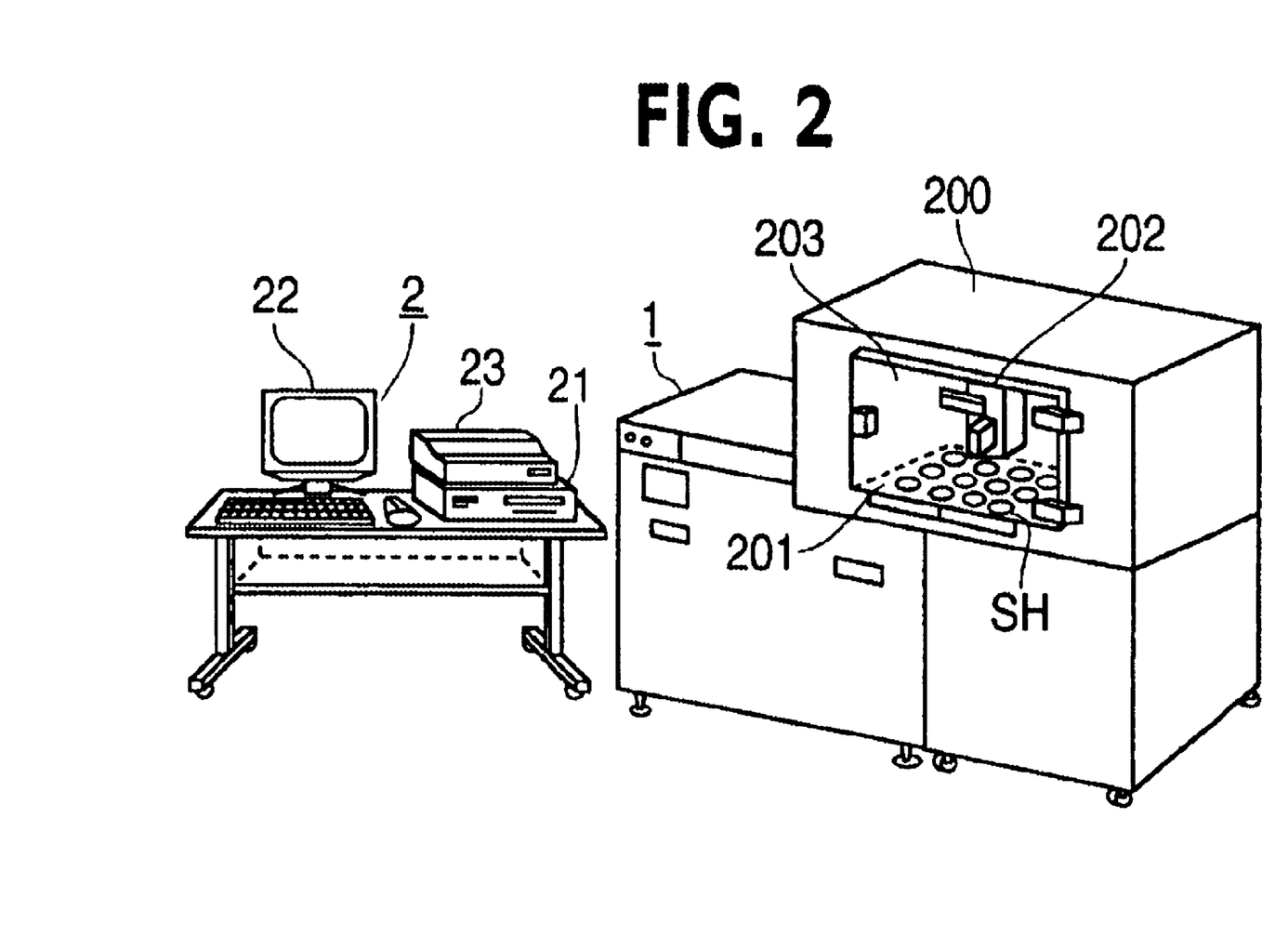
FIG. 2 is a perspective view for showing a total outlook structure of the fluorescence X-ray analyzer according to the embodiment of the present invention.

First of all, FIG. 2 shows the total structure of an analyzing apparatus according to an embodiment of the present invention, wherein samples will be analyzed automatically while being mounted into a sample chamber, and in particular, in a fluorescence X-ray analyzer, as one example thereof, wherein constituent components of substance can be analyzed by means of the fluorescence X-rays obtained, by irradiating X-rays upon the surface of each of the samples mounted within the sample chamber, at high accuracy.

Namely, in the FIG. 2 mentioned above, a reference numeral 1 depicts the fluorescence X-ray analyzer mentioned above, and though not shown in the figure, in a vacuum chamber inside thereof are provided the sample chamber into which the samples to be measured are mounted, a X-rays tube (i.e., X-rays generator device) for generating X-rays to be irradiated upon the samples mounted within the vacuum analysis chamber, a spectroscopic means including a analyzing crystal for analyzing the fluorescence X-rays generated from the samples, a detection portion constructed with, such as, a scintillation counter or X-rays detectors, for detecting the X-rays analyzed through the spectroscopic means, and so on. Even though not illustrated herein, it is needless to say that there are further provide a vacuum exhaust system for maintaining an inside of the vacuum chamber of the above-mentioned analysis apparatus under vacuum condition, various sensors, and valves, etc.

In a part of the main body of the fluorescence X-ray analyzer 1 mentioned above, in particular in an upper portion thereof in the present embodiment, there is provided a sample exchanger portion (ormachine) 200 for enabling automatization (or unmanning) of the sample analysis by the analyzing apparatus. Inside the sample exchanger portion 200, as shown in the figure, a large number of sample holders SH are aligned on a sample table 201, and further in inside thereof is provided a transfer mechanism 202 with a robot arm for transferring the sample holders SH mentioned above into and/or from the sample chamber of the analyzing apparatus 1, sequentially.

Herein, the sample holder SH, a large number of which are aligned on the sample table 201, means something for holding the sample to be analyzed therebetween on an upper portion of a metallic member having an about cylinder-like outer configuration, and for enabling the X-rays to be irradiated upon the sample through an opening formed at an upper end-surface thereof. On a sample loading portion (i.e., an opening portion on a front of the exchanger), i.e., an opening being formed between an inside and an outside of the sample exchanger portion 200, a transparent cover 203 made of, such as, a transparent glass plate, or the like, is attached to be opened or closed freely. The samples, analysis of which will be automated (or unmanned) by means of the analyzing apparatus mentioned above, mounted onto the sample holders SH to be aligned on the sample table 201, and thereafter are positioned within an inside of the sample exchanger portion 200, while the cover 203 being opened. And then, the cover is closed to start the analysis operation thereof.

Also, the fluorescence X-ray analyzer 1 is connected with a data processing computer 2, being constructed with, for example, a personal computer, etc., as a calculation-processing portion, through a data communication circuit not shown herein, so that they can communicate data with each other freely. Herein, the data processing computer 2 constructing the calculation-processing portion receives analysis results of the samples, which are measured by means of the analyzing apparatus mentioned above, in the main body 21 thereof, and it prepares desired analysis data by treating or processing with predetermined data processing thereupon. Those will be displayed on a display screen (i.e., a display device) 22, or outputted through an output device, such as a printer 23, etc.

Figure 1:
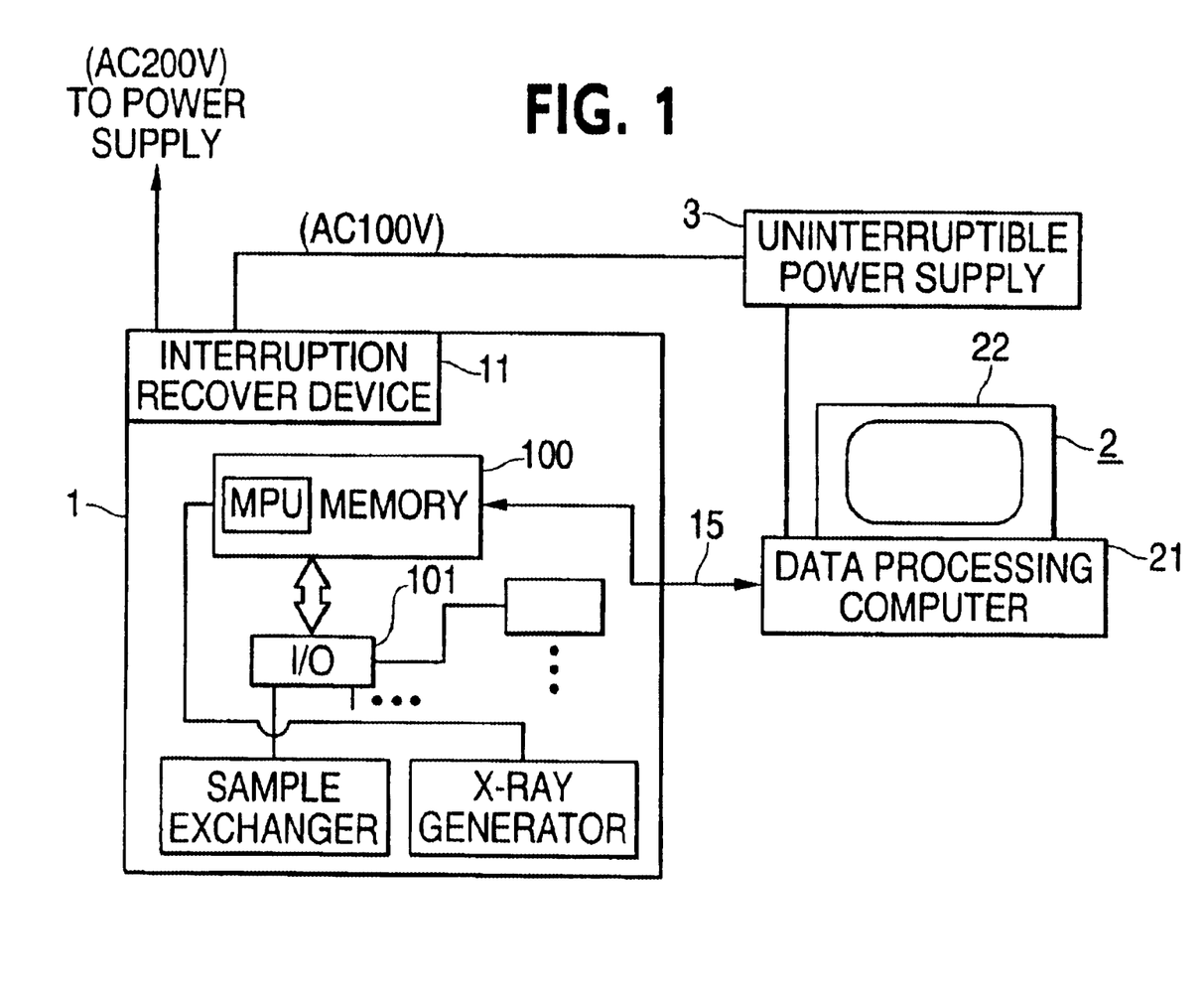
FIG. 1 is a circuit block diagram for showing an example of the structure of an electric power circuit, including a data processing computer therein, in a fluorescence X-ray analyzer according to an embodiment of the present invention.

Next, in FIG. 1 is shown an example of the circuit structure of an electric power supply or source for those, including the fluorescence X-ray analyzer 1 mentioned above and the data processing computer 2 therein. As apparent from the figure, inside the fluorescence X-ray analyzer 1, an electric interruption recover device 11 is provided, in particular, within an electric power supply portion thereof, wherein the analyzer 1 is connected with a commercial electric power supply of AC 200 V, for example, via the interruption recovery device 11, so as to be supplied with necessary electric power. On a while, the data processing computer 2 constructed with, such as, a personal computer, etc., is electrically connected with the electric power source of AC 100 V, the output voltage thereof being lowered or stepped down by the function of the interruption recovery device 11 mentioned above, i.e., through an uninterruptible power supply (UPS) 3 for use in the personal computer, being provided on the way, which is constructed with a capacitor having large capacity, for example. Further, a reference numeral 15 herein indicates the data communication for connecting between the fluorescence X-ray analyzer 1 mentioned above and the data processing computer 2.

Further, the fluorescence X-ray analyzer 1 comprises, as shown in the figure, a computer 100 for use in control within inside thereof, and the computer 100 for use in control is constructed with, including a MPU (Micro Processing Unit) and/or various kinds of memories therein. Also, the controller 100 inputs or receives detection signals from various kinds of detectors of the analyzing apparatus 1 through an I/O unit (Input Output unit) 101, and it outputs or provides drive/control signals to various driving and controlling systems, including the sample exchanger and/or the X-ray generator. Also, the computer 100 for use in control is connected between the data processing computer 2 mentioned above, via a communication network 15, including a LAN (Local Area Network), etc, thereby being constructed so that they can communicate information including the data and the instructions, with each other. With such the construction, an operator of the analyzing apparatus can indicate a desired analysis operation from an inputting means provided on the side of the data processing computer 2, and then, the computer 100 for use in control receiving the instruction from the data processing computer 2 performs the drive/control operations along with predetermined sequences upon the various kinds of the detectors and/or the driving/controlling systems, thereby achieving the analysis operation by means of the analyzing apparatus, and further the control operation of the sample exchanger portion which enables the automatization (or unmanning) of analysis of the samples.

Also, the data processing computer 2 mentioned above further comprises an inputting means, such as a keyboard and/or a mouse, etc., as the input device, in addition to the printer 23, the main body 21, and the display device 22, and furthermore, it is needless to say, but within an inside of the main body 21 are provided a central processing unit (CPU) for executing predetermined calculation processes therewith, and/or memories means, such as of RAM or/and a hard disc apparatus, etc.

Figure 3:
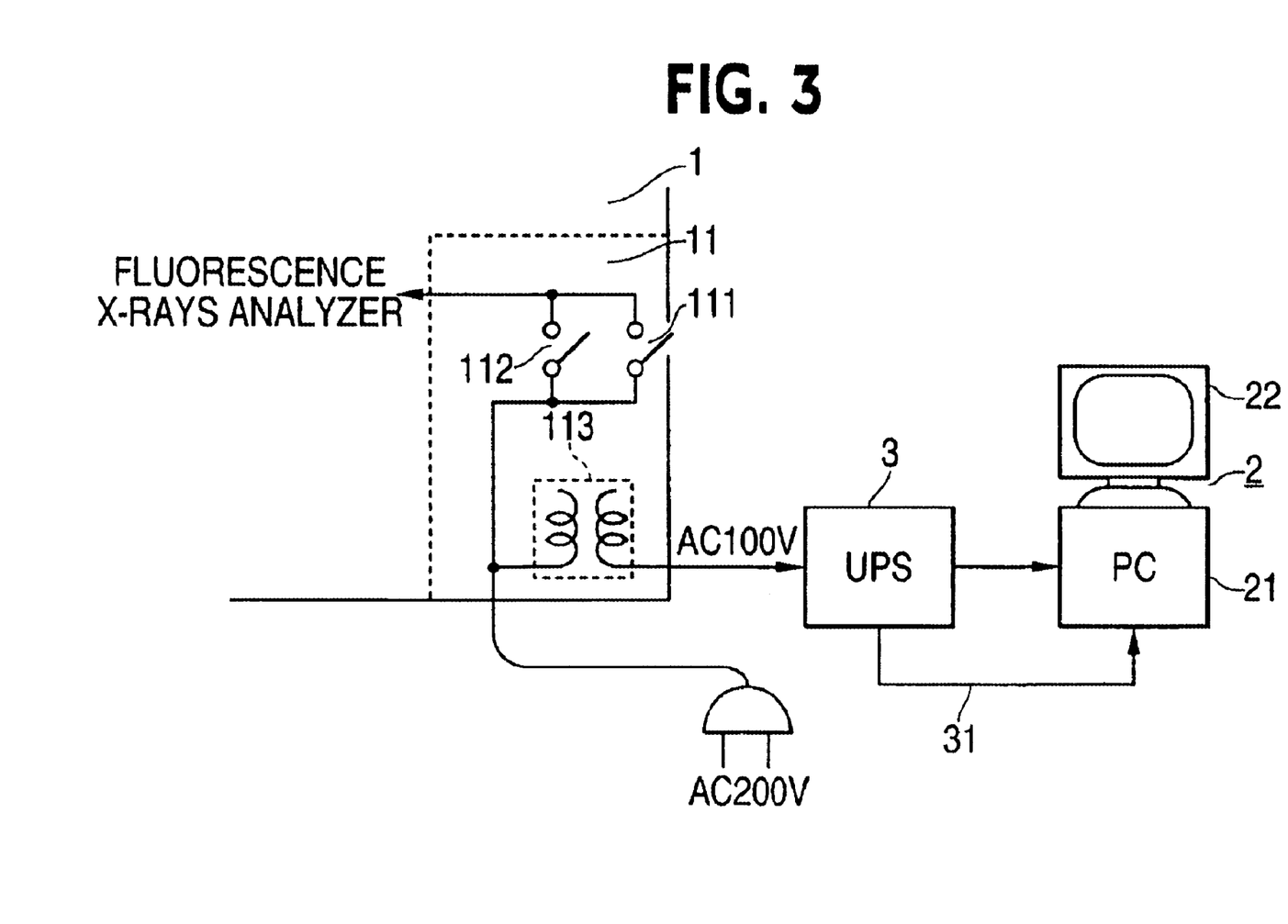
FIG. 3 is a circuit diagram for showing an example of the structure inside a power interruption-recovering device in the fluorescence X-ray analyzer mentioned above.

Next, FIG. 3 shows an example of the interior structure of the interruption recover device 11 mentioned above. As apparent from the figure, the commercial electric power source AC 200 is supplied to each part of the fluorescence x-ray analyzer 1, through a power switch (i.e., a switch for turning on or establish the operation power source onto the apparatus) 111 and a latching relay 112, being disposed in parallel with each other, thereby supplying necessary electric energy to each part of the apparatus. A part of the power source of AC 200 V is lowered or stepped down in voltage down to a predetermined voltage (for example, 100 V) through a step-down transformer 113, for example, and is supplied to the uninterruptible power supply (UPS) 3 for use in the computer. In this manner, the data processing computer 2 is supplied with the electric power from the uninterruptible power supply (UPS) 3 for use in the computer, therefore, it will be supplied with necessary electric power or energy for the operation thereof, for a predetermined time period, even if the stoppage or the interruption occurs in the commercial electric power source of AC 200 V mentioned above. Further, the uninterruptible power supply (UPS) 3 for use in the computer comprises a function of detecting the stoppage or the interruption and/or the recovery of electricity in the input electric power, and the detected signal of the stoppage or the interruption and/or the recovery are/is transmitted to the data processing computer 2 through the data communication circuit 31, such as of a RS232C, etc.

Figure 4:
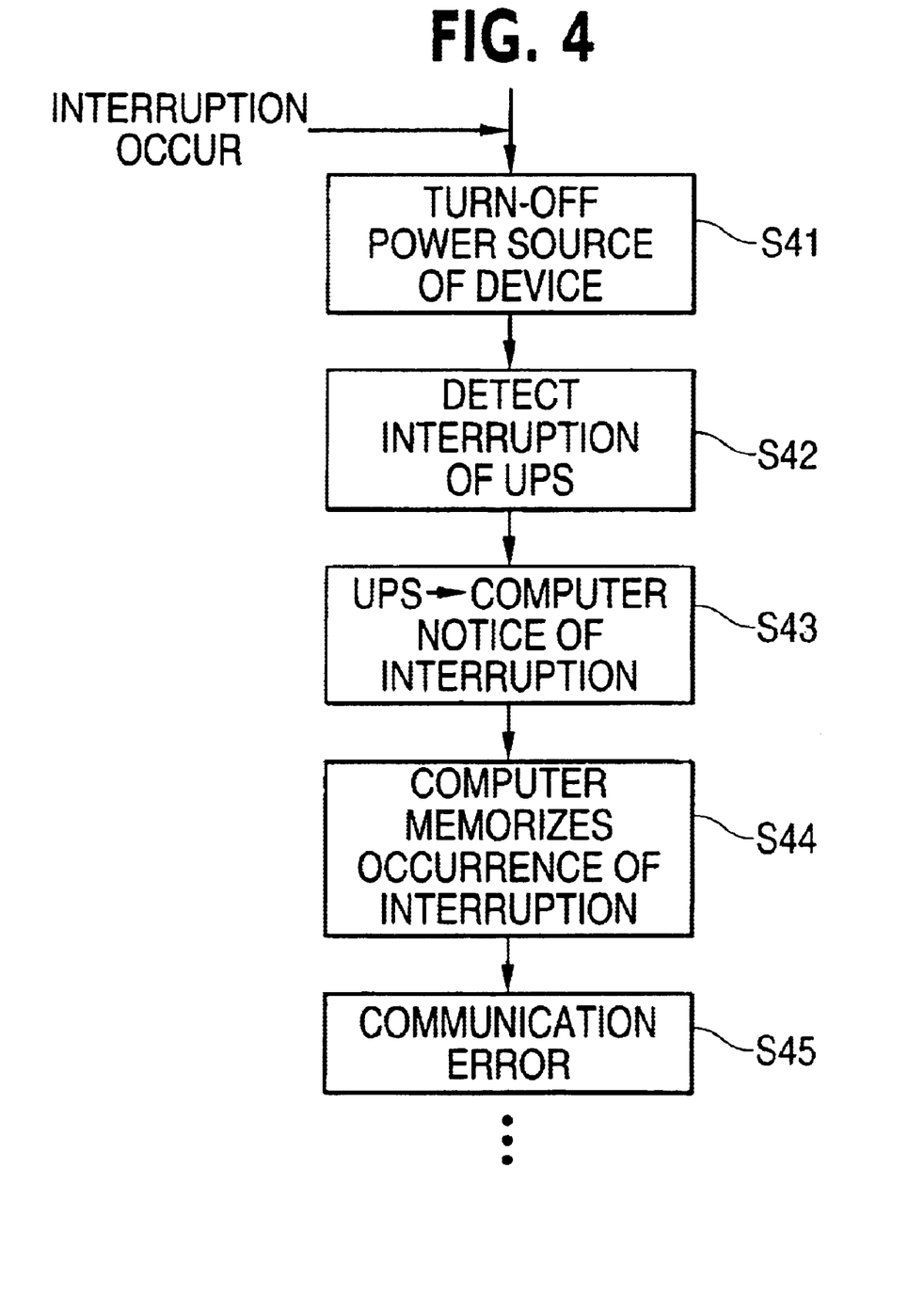
FIG. 4 shows a flowchart for explaining operations when the power interruption occurs in the fluorescence X-ray analyzer mentioned above.
Figure 6:
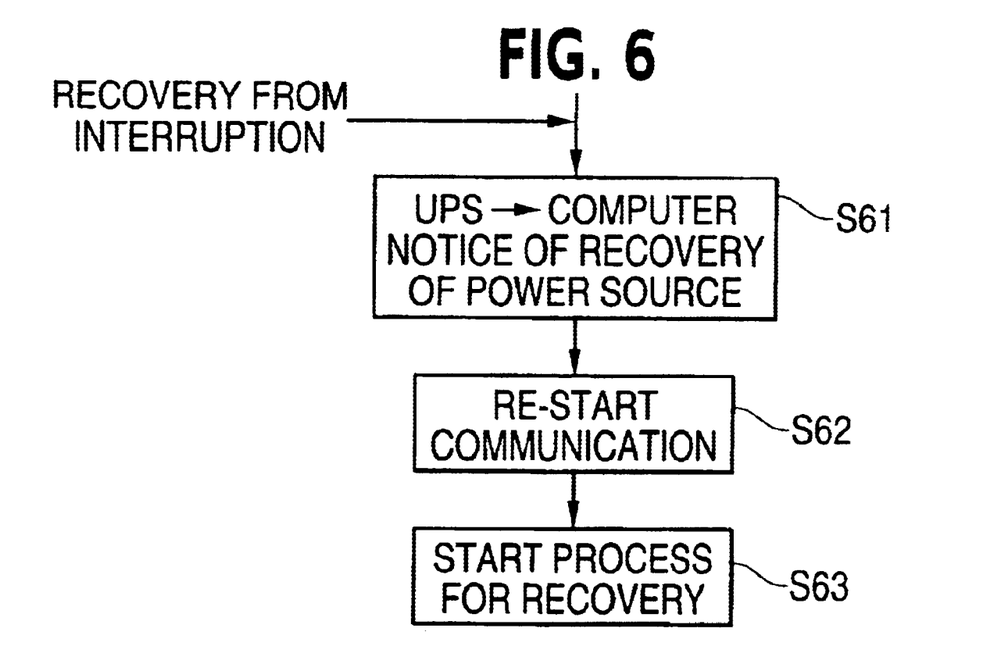
FIG. 6 shows a flowchart for explaining operations when the electricity is recovered from the interruption thereof in the fluorescence X-ray analyzer mentioned above.
Figure 7:
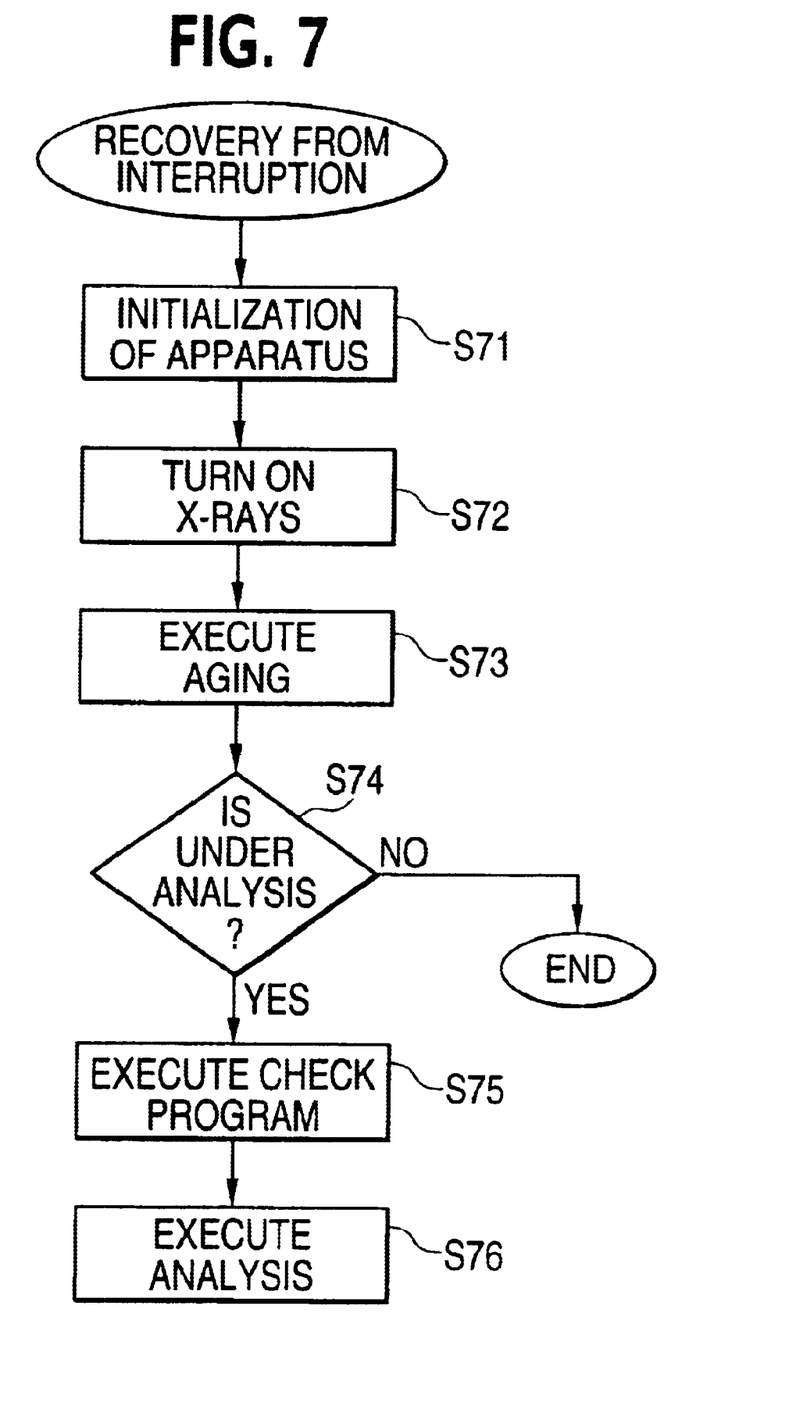

Following the above mentioned, operations of the fluorescence X-ray analyzer 1 including the data processing computer 2, according to the present invention, mentioned in details of the structure thereof in the above, will be explained in more details thereof, by refereeing to a flowchart shown in FIGS. 4, 6 and 7 attached thereto.

First, when the interruption occurs, the fluorescence X-ray analyzer 1 stops the operations of the fluorescence X-ray analyzer itself and the various mechanical portions thereof, and further the computer 100 for use of control, as well, since the power source thereof is stopped or interrupted. On a while, as shown in the FIG. 4, the power switch 111 provided on the side of the fluorescence X-ray analyzer 1 is turned into open (i.e., OFF) condition (in a step S41). Following this, the uninterruptible power supply (UPS) 3 detects the interruption of electricity (in a step S42), and this fact is informed to the data processing computer 2 through the data communication circuit 31, such as of the RS232C mentioned above (in a step S43). However, since the data processing computer 2 obtains or fed with the electric power thereof from the uninterruptible power supply (UPS) 3, it responds to the information without stoppage in the operation, thereby memorizing or storing the fact of occurrence of the stoppage or the interruption into the memory thereof (in a step S44). After that, since the computer 100 for use in control of the fluorescence X-ray analyzer 1 stops the operation thereof due to the stoppage or the interruption of electricity, a communication error will occur at the side of the data processing computer 2 when trying to send information during the interruption of electricity, for example,(in a step S45).

However, since it is possible to ascertain the occurrence of the stoppage or the interruption due to the communication error, which is detected at the side of the data processing computer 2, this may be displayed on the screen of the display device 22.

Further, the data processing computer 2 is always, not only watching or observing contents of the analysis operations, but also memorizing them into the memory thereof. An example of the memorized contents of analysis operation will be shown in FIG. 5. Namely, for the purpose of showing the predetermined analysis operations executed by the analyzing apparatus 1, while indicating "Operation SQ (Sequence)" with "Sample Position" at that time, "Analysis Code" and "Contents" thereof, status of that operation is indicated in the column of "Status" disposed at a head of each of the operations. Herein, in the present example, "1" indicates that the operation is completed (finished), while "0" that the operation is under executing condition when the interruption occurs. In the step S44 mentioned above, the contents of the analysis operation when the interruption occurs is also maintained into the memory, at the same time when memorizing the stoppage or the interruption into the memory.

Next, explanation will be given below, about operations when the power source is recovered to feed electricity after the occurrence of the stoppage or the interruption thereof, in the fluorescence X-ray analyzer 1 including the data processing computer 2 therein.

First when the electricity is recovered from the stoppage or the interruption thereof, still the uninterruptible power supply (UPS) 3 detects the recovery of the power source, and notices that fact to the data processing computer 2 through the data communication circuit 31, such as of the R232C, etc. (in a step S61). With this recovery, since also the computer 100 for use in control at the side of the analyzing apparatus 1 recovers or re-starts the operation, it starts communication between the data processing computer 2 (in a step S62). Therefore, the data processing computer 2 instructs the computer 100 for use in control at the side of the analyzing apparatus 1, to start a processing for recovering from the stoppage or the interruption of electricity (in a step S63).

An example of the processing for recovering from the stoppage or the interruption will be explained by referring to, for example, the flowchart shown in FIG. 7. Thus, upon the recovery from the stoppage or the interruption (for example, a notice of recovery of electricity, obtained from the uninterruptible power supply (UPS) 3), first, supply of electricity will be conducted onto the analyzing apparatus 1 through the latching relay 112 which is closed in advance, thereby executing initialization of apparatus upon the fluorescence X-ray analyzer 1 (in a step S71). After completion of the initialization of apparatus, the X-rays tube, as the X-ray generator in the apparatus, is turned into ON condition (in a step S72), and further is executed with an aging process thereupon, so as to be set at the normal tube voltage and current thereof (in a step S73). Also, but not shown in the figure, it is possible to conduct adjusting operations for the analyzing apparatus herein, such as, adjustment of a PHA (Pulse Height Analyzer) etc., according to the contents presented in advance, by appointment thereof. Thereafter, by referring to, for example, the information memorized in the memory device by the data processing computer 2 when the interruption occurs, i.e., the contents of the analysis operations in the analyzing apparatus when the interruption occurs, as shown in the FIG. 5, it is determined whether the analyzing apparatus 1 is under the analysis operation or not when the interruption occurs (in a step S74).

Then, as a result of the decision made in the step S74 mentioned above, if the analyzing apparatus is not under the analysis operation when the interruption occurs (i.e., in case of "No"), the processing is finished, as shown in the figure. On the contrary to this, if deciding that the analyzing apparatus is under the analysis operation (i.e., in case of "Yes") as a result of the decision made in the step S74, the step is shifted or moved to the following process of executing a check program (in a step S75), and thereafter followed by execution of the analysis operation (in a step S76).

Figure 5:
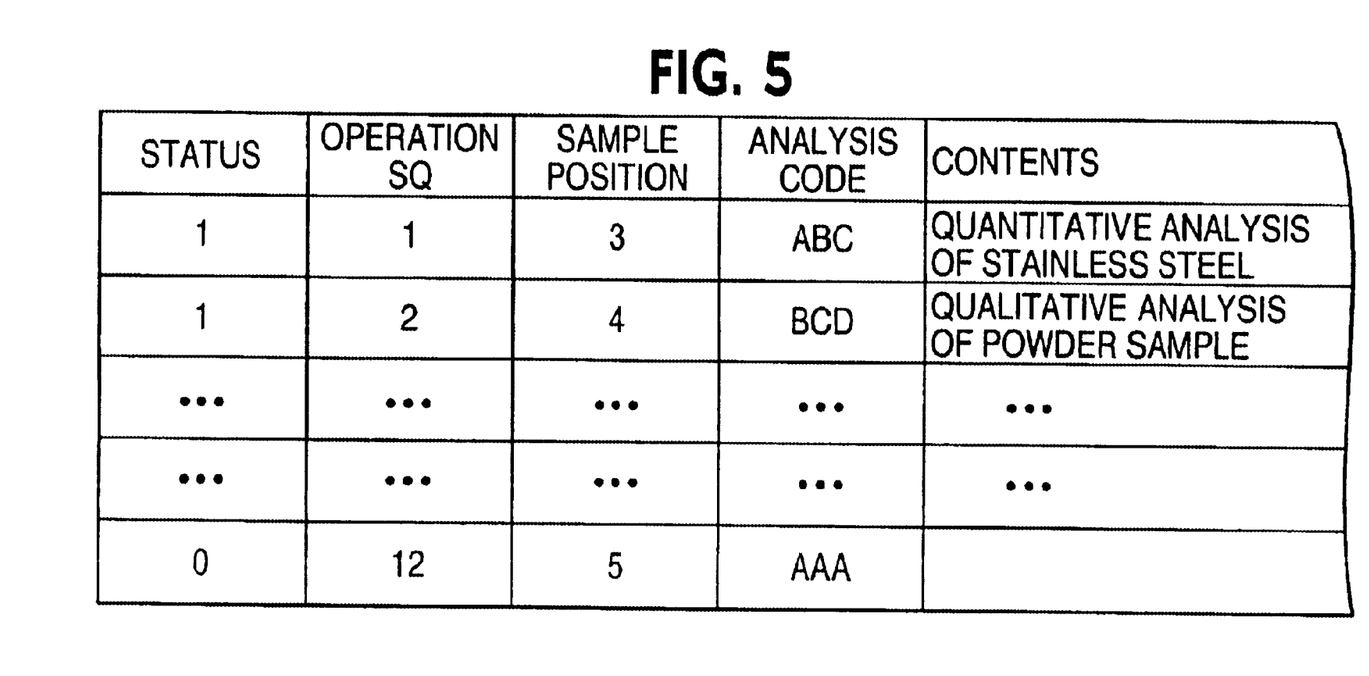
FIG. 5 is a view for showing an example of information, which a data processing computer will stores within a memory device when the power interruption occurs, in the fluorescence X-ray analyzer mentioned above.

However, by utilizing the contents of analysis operation shown in the above FIG. 5, in this time, in particular, the column of the "Status" thereof, it is possible to know how far the analysis was completed or advanced in the analysis operations by the apparatus, and at which "Operation SQ" the analysis is stopped or interrupted when the interruption occurs.

This means that, when the analysis operation is started again by the step S76 mentioned above, it is possible to begin with the analysis from the "Operation SQ", following the "Operation SQ" which was already completed before the occurrence of the interruption, i.e., excepting the "Operation SQ" completed (thus, those, the column "Status" of which are "1"). In more details of the example shown in the above FIG. 5, it starts the analysis operation from the "Operation SQ" of "12", in which it is "0" in the "Status" column thereof.

This is effective, in particular, for the fluorescence X-ray analyzer, performing the unmanned operations (analysis), continuously, for long time, while exchanging a large number of samples with using the automatic sample exchanger or the like, in an unmanned manner. Namely, according to the conventional fluorescence X-ray analyzer, in the case where the stoppage or the interruption of electricity occurs on the way of analysis operations, a series of analysis operations, starting with the initialization of the apparatus, must be executed, again, from the beginning thereof, when the electricity is recovered therefrom. However, with the fluorescence X-ray analyzer according to the present invention, the operation will start from the analysis operation, without executing those that were completed previously again, but just following thereto, therefore it is possible to shorten or reduce the time necessary for analysis, greatly, in particular, in the case where the stoppage or the interruption occurs on the way of the analysis operations.

Furthermore, the explanation was given only upon the example of the fluorescence X-ray analyzer according to the embodiment mentioned above, in which the said analyzing apparatus 1 and the data processing computer 2 are constructed separately. However, the present invention should not be restricted only to such the structure, and it is also possible to provide the analyzing apparatus 1 and the data processing computer, together, within the same housing.

As also apparent from the detained description given in the above, according to the present invention, the electric power source of the apparatus will be turned on, automatically, so as to recover the analysis operation back to that at the time when the interruption occurs, even when the stoppage or the interruption of electricity occurs during the analysis operation and thereafter when the power source recovers from, whereby continuity of the analysis operations is ensured, and thereby duplication in the analysis operations when the stoppage or the interruption occurs during the analysis operations can be reduced greatly, therefore it is possible to achieve a superior effect of providing the analyzing apparatus, in particular, being suitable for conducing analysis by unmanned operation.

While we have shown and described several embodiments in accordance with our invention, it should be understood that the disclosed embodiments are susceptible of changes and modifications without departing from the scope of the invention. Therefore, we do not intend to be bound by the details shown and described herein but intend to cover all such changes and modifications falling within the ambit of the appended claims.

What is claimed is:

1. An analyzing apparatus able to analyze samples automatically, by transferring the samples into an analysis chamber, sequentially, comprising:

an interruption recovering means for automatically turning on an electric power supply for the analyzing apparatus, when electricity is re-establishing after instantaneous interruption thereof; and a calculation processing portion, being connected through an uninterruptible power supplying means to said electric power supply, for always supervising analysis contents of said analyzing apparatus, wherein, said calculation processing portion includes means for temporality memorizing the analysis contents in said automatic analyzing apparatus when the instantaneous interruption occurs, and further means for supplying electricity to said analyzing apparatus through said interruption recovering means and for restarting the analysis of the samples upon basis of the memorized analysis contents the instantaneous interruption occurs, when the electricity is recovered; and an X-ray tube, wherein said calculation processing portion further comprises means for executing aging of said X-rays tube after turning on said electric power supply when the electricity is recovered after the interruption thereof.

2. An analyzing apparatus as defined in the claim 1, wherein said calculation processing portion further comprises means for executing initialization of said automatic analyzing apparatus, after automatically turning on said electric power supply onto said analyzing apparatus when the electricity is recovered.

3. An analyzing apparatus as defined in the claim 2, wherein said calculation processing portion further comprises means for conducting setting operation for said analyzing apparatus after execution of the initialization of said automatic analyzing apparatus.

* * * * *